United States Patent [19]

Matsuura et al.

[11] Patent Number: 4,652,849

[45] Date of Patent: Mar. 24, 1987

[54] GAS SENSOR

[75] Inventors: Toshitaka Matsuura; Teppei Ohkawa; Keizo Furusaki; Akio Takami, all of Nagoya, Japan

[73] Assignee: NGK Spark Plug Co., Ltd., Nagoya, Japan

[21] Appl. No.: 695,361

[22] Filed: Jan. 28, 1985

[30] Foreign Application Priority Data

Jan. 30, 1984 [JP] Japan ................................ 59-14653

[51] Int. Cl.$^4$ ............................................. H01L 7/00
[52] U.S. Cl. ........................................... 338/34; 73/23; 73/28 R; 422/90; 422/98; 422/108; 136/224; 136/225
[58] Field of Search ................. 338/34, 35; 136/224, 136/225; 422/108, 98, 168, 95, 90; 73/23, 28 R

[56] References Cited

U.S. PATENT DOCUMENTS

| | | | |
|---|---|---|---|
| 3,906,721 | 9/1975 | Micheli et al. | 136/224 |
| 3,989,614 | 11/1976 | Tien | 338/34 X |
| 4,029,472 | 6/1977 | Micheli et al. | 136/225 X |
| 4,416,763 | 11/1983 | Fujishiro | 338/34 X |
| 4,453,151 | 6/1984 | Leary et al. | 338/34 |
| 4,507,643 | 3/1985 | Sunano et al. | 338/34 |

Primary Examiner—E. A. Goldberg
Assistant Examiner—M. M. Lateef
Attorney, Agent, or Firm—Fleit, Jacobson, Cohn & Price

[57] ABSTRACT

A gas sensor has a 100–400 μm thick gas-sensitive layer containing 5–30 mole % of a platinum group metal or an alloy thereof.

7 Claims, 16 Drawing Figures

GAS SENSOR

BACKGROUND OF THE INVENTION

1. Field of the Invention

This invention relates to a gas sensor, and more particularly to a gas sensor having a high resistivity against lead.

2. Description of the Prior Art

It has been known to detect the presence and concentration of a gas in air by a gas sensor which uses a gas-sensitive element made of an oxide semiconductor, such as tin oxide ($SnO_2$), zinc oxide (ZnO), titania ($TiO_2$), cobalt oxide (CoO), and the like, whose electric resistance varies upon exposure to the air. To simplify the structure of such gas-sensitive element for improving the productivity thereof, the so-called hybrid techniques has been developed; for instance, by printing both the gas-sensitivity element and electrodes therefor in the form of thick films on an electrically insulating ceramic substrate. It is also known that the characteristics, especially the temperature characteristics, of such gas-sensitive element can be improved by adding a platinum group element such as platinum black therein.

When the gas sensor of the prior art is used, for instance, for the detection of air fuel ratio in internal combustion engines using leaded gasoline, the gas-sensitive element of the sensor is apt to be deteriorated by lead contained in the engine exhaust gas. Such deterioration causes a shortcoming of the gas sensor in that satisfactory gas sensitivity cannot be ensured.

SUMMARY OF THE INVENTION

Therefore, an object of the invention is to obviate the above-mentioned shortcoming of the prior art by providing an improved gas sensor which has a high lead resistivity, so that excellent gas-sensitive characteristics can be ensured regardless of the presence of lead in the gas being sensed.

In a preferred embodiment of the gas sensor according to the invention, a pair of electrodes are formed on an electrically insulating ceramic substrate, and lead wires extend from the electrodes to the outside of the gas sensor. A 100–400 µm thick gas-sensitive layer is formed on the ceramic substrate so as to sandwich the electrodes between the gas-sensitive layer and the substrate. The gas-sensitive layer contains 5–30 mole % of a platinum group element and/or an alloy of platinum group elements. The electric resistance of the gas-sensitive layer to be measured by the electrodes, varies depending on the kind and the concentration of a specific gas in atmosphere that is in contact with the gas-sensitive layer.

The ceramic substrate to be used in the gas sensor of the invention can be a regularly used substrate. For instance, it can be a sintered ceramic substrate mainly consisting of alumina, beryllia, mullite, steatite, and the like. The electrodes can be made of electrically conductive material which withstands the sintering temperature of the ceramic substrate. Conductors mainly consisting of gold or platinum group elements is usually used, and platinum is particularly suitable for the electrodes in the gas sensor of the invention, because platinum has an electric resistance suitable for a heater and it can be used directly in the electric circuit without modification.

The platinum group element to be contained in the gas-sensitive layer can be iridium, palladium, ruthenium, rhodium, osmium, and the like. From the standpoint of heat resistance, cost, and catalytic activity, the use of platinum is most preferable. The major ingredient of the gas-sensitive layer is preferably an oxide semiconductor, such as tin oxide ($SnO_2$), titania ($TiO_2$), cobalt oxide (CoO), zinc oxide (ZnO), niobium oxide ($Nb_2O_5$), chromium oxide ($Cr_2O_3$), and the like. From the standpoint of heat resistance, tin oxide and titania are preferable, and the use of titania is most preferable.

The reason for restricting the concentration of a platinum element in the gas-sensitive layer to 5–30 mol % and the thickness of the gas-sensitive layer to 100–400 µm is to improve the resistivity of the gas-sensitive layer against lead. More particularly, if the gas-sensitive layer contains less than 5 mol % of a platinum group element or is thinner than 100 µm, the layer is apt to be deteriorated by lead contained in the gas being measured so that the gas-sensing characteristics of the layer becomes inferior. On the other hand, if the gas-sensitive layer contains more than 30 mole % of a platinum group element or is thicker than 400 µm, the response of the layer becomes too slow.

Unless the temperature of the gas-sensitive layer is higher than a certain level, satisfactory gas-sensing characteristics cannot be achieved. Accordingly, when the ambient temperature is expected to be low, the gas-sensitive layer must be heated, for instance by a heater or the like. From the standpoint of making the gas sensor small and providing for a high productivity, it is preferable to mount a heater layer on the ceramic substrate of the gas sensor. To avoid deterioration of the lead resistivity, the heater layer, if used, should be capable of heating the gas-sensitive layer during operation at a temperature above 500° C.

BRIEF DESCRIPTION OF THE DRAWINGS

For a better understanding of the invention, reference is made to the accompanying drawings, in which.

Throughout different views of the drawings, 10 is a gas sensor, 11 is a gas-sensitive layer, 12 is a body hardware, 13 is a protector, 14 is an inner cylinder, 15 is a spacer, 16 is a filler powder, 17 is a glass seal, 18 is a gasket, 19 is an outer cylinder, 20 is a sealing, 21 through 23 are lead wires, 24 through 26 are compressible connectors, 31 through 33 are terminals, 40 is a ceramic substrate, 41 is a ceramic cover layer, 42 and 43 are electrodes, 44 is a heater layer 45 through 47 are end portions, 48 through 50 are platinum lead wires, 51 is an opening, 52 represents granulated spherical ceramic particles, 60 is an internal combustion engine, 61 is an exhaust manifold, 65 is a control unit, 67 is an air fuel ratio meter, 69 is a recorder, 70 is a battery, 72 is the resistance of the heater layer, 74 is the resistance of the gas-sensitive layer, 76 is a current-detecting resistance, and 78 is a CPU.

DESCRIPTION OF THE PREFERRED EMBODIMENTS

The details of the structure and the manufacturing process of the gas sensor of the invention will be described now by referring to an embodiment which is an oxygen sensor for detecting the oxygen concentration in exhaust gas from an internal combustion engine. Performance test of the gas sensor of the invention will be also described by referring to experiments in which the above oxygen sensor is actually mounted on the internal combustion engine for controlling the air fuel ratio.

Figure 1:
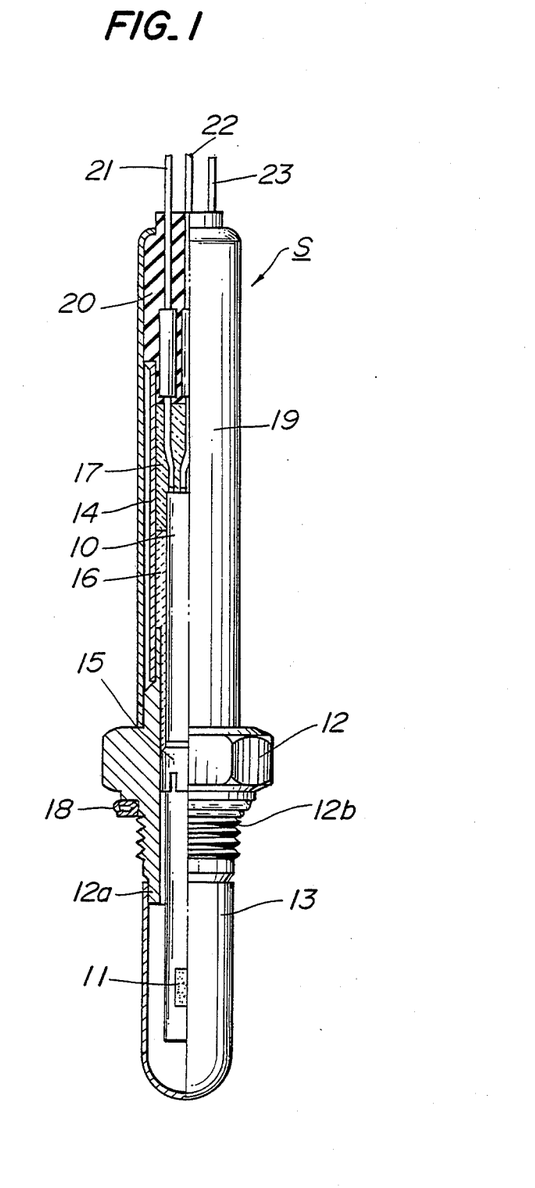
FIG. 1 is a partially cutaway overall side view of an oxygen detector having an oxygen sensor of the invention mounted therein.

In FIG. 1, showing a partially cutaway overall side view of an oxygen detector S, a gas sensor 10 as an embodiment of the invention has a gas-sensitive layer 11 formed on a ceramic substrate. The gas sensor 10 of this embodiment acts to detect the oxygen concentration of a gas being monitored. A cylindrical body hardware 12 houses the gas sensor 10 therein and is mountable on an internal combustion engine. A protector 13 is coupled to the engine-side end 12a of the body hardware 12, so as to protect the gas sensor 10. The gas sensor 10 is held by an inner cylinder 14 with a spacer 15 inserted therebetween, which inner cylinder 14 is carried by the body hardware 12. Filler powder 16 and glass seal 17 are stuffed between the gas sensor 10 and the inner cylinder 14, so as to keep the gas sensor 10 in position. To facilitate the mounting of the oxygen detector S to an engine, the body hardware 12 has a threaded portion 12b. Thus, the oxygen detector S can be screwed to the engine with a gasket 18 disposed between the body hardware 12 and the screwed portion of engine wall, so as to prevent engine exhaust gas from leaking through the screwed portion.

The filler powder 16, which is preferably a powder mixture consisting of talc and glass at a ratio of 1:1, acts to fix the gas sensor 10 in position within the inner cylinder 14. The glass seal 17 stuffed in the inner cylinder 14, which seal is preferably made of glass with a low melting point, acts to prevent the gas being monitored from leaking and to protect terminals of the gas sensor 10. To this end, the glass seal 17 covers and holds both a part of the gas sensor 10 and joints of the terminals with platinum lead wires to be described hereinafter.

Figures 2, 3:
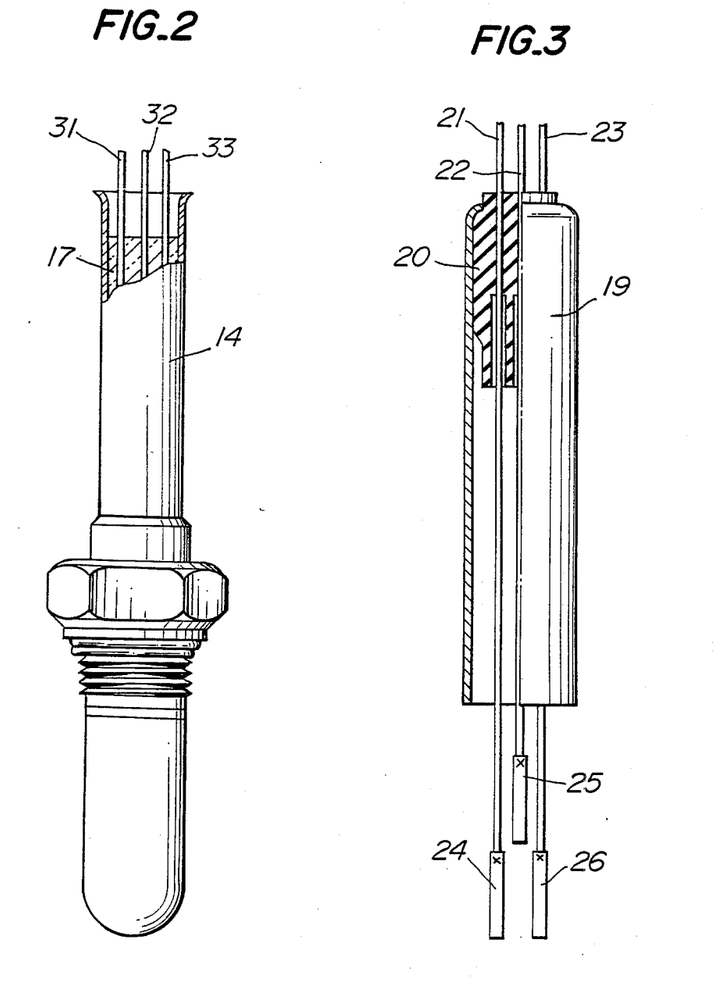
FIG. 2 is a partially cutaway side view of an inner cylinder of the oxygen detector, showing terminals extending outward from glass seal of the inner cylinder.
FIG. 3 is a partially cutaway side view of an outer cylinder of the oxygen detector, showing the manner in which one end of the outer cylinder is closed by a sealing before it is coupled with the inner cylinder.

An outer cylinder 19 is coupled to the body hardware 12 so as to cover the inner cylinder 14. A sealing 20 made of silicone rubber is stuffed between the inner cylinder 14 and the outer cylinder 19, so as to protect and insulate both outgoing lead wires 21 through 23 and their joints with the terminals 31 through 33 of the gas sensor 10 projecting from the glass seal 17 as shown in FIG. 2. To facilitate the joining of the lead wires 21 through 23 with the terminals 31 through 33, the sealing 20 and the lead wires 21 through 23 may be placed in the inside of the outer cylinder 19 beforehand, and compressible connectors 24 through 26 may be joined to the inner ends of the lead wires 21 through 23 respectively, as shown in FIG. 3. Then, the terminals 31 through 33 of the gas sensor 10 may be joined to the other ends of the connectors 24 through 26 respectively.

The inventors prepared samples of the gas sensor 10 by a process as shown in the plan views of FIG. 4A through FIG. 7A. FIG. 4B through FIG. 7B show sections taken along the lines with arrows B in FIG. 4A through FIG. 7A respectively.

Green sheets for ceramic substrates 40 and ceramic cover layers 41 were formed in the following manner: Namely, 100 parts by weight of powder mixture was prepared by mixing 92% by weight (wt%) of alumina ($Al_2O_3$) with a mean diameter of 1.5 $\mu$m, 4 wt% of silica ($SiO_2$), 2 wt% of calcia ($CaO_2$), and 2 wt% of magnesia (MgO); 12 parts by weight of butyral resin and 6 parts by weight of dibutyl phthalate (DBP) were added to the 100 parts by weight of the powder mixture; a slurry was made by mixing the powder mixture in an organic solvent; and the green sheets were formed from the slurry by using a doctor blade. The green sheet for the ceramic substrate 40 was 1 mm thick, while the green sheet for the cover ceramic layer 41 was 0.3 mm thick.

Layers for electrodes 42, 43 and a heater layer 44 were printed in the form of thick film patterns, by using a platinum paste made by adding 7% of alumina ($Al_2O_3$) based on the amount of platinum. The electrodes 42 and 43 are for measuring the electric resistance of the above-mentioned gas-sensitive layer 11, and the heater layer 44 is for heating the gas-sensitive layer 11. End portions 45 through 47 are for applying an electric current to the heater layer 44 and extracting the output signal from the gas-sensitive layer 11.

Figure 4A:
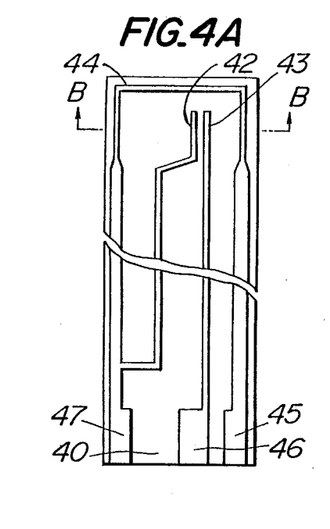
FIG. 4A, FIG. 5A, FIG. 6A and FIG. 7A are schematic plan views, showing the process in which a gas sensor of the invention is assembled.
Figure 4B:
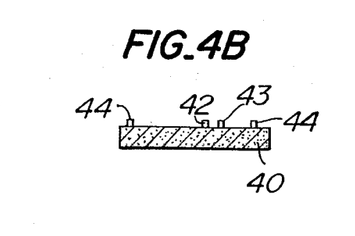
FIG. 4B, FIG. 5B, FIG. 6B and FIG. 7B are sectional views taken along the lines with arrows B in FIG. 4A, FIG. 5A, FIG. 6A and FIG. 7A, respectively.
Figure 5A:
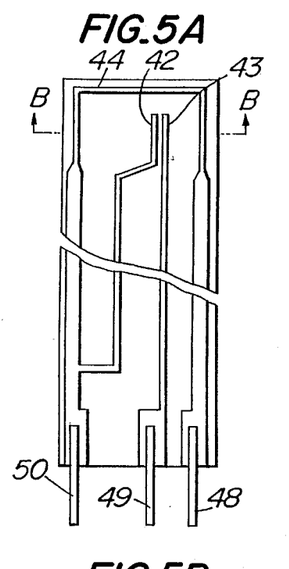

In preparing the gas sensor 10, patterns for the electrodes 42, 43 and the heater layer 44 were at first printed on the green sheet for the ceramic substrate 40 together with their end portions 45 through 47 by using the platinum paste, a shown in FIG. 4A and FIG. 4B. Thereafter, platinum lead wires 48 through 50 with a diameter of 0.2 mm were disposed on the end portions 45 through 47 of the patterns respectively, as shown in FIG. 5A. In printing the platinum paste patterns, four kinds of the heater layers 44 with different widths of the patterns therefor were provided. Thus, when the temperature of gas being monitored was 200° C., the gas-sensitive layer 11 of the completed gas sensor 10 assumed four different temperatures depending of the kind of the heater layer pattern used therein, i.e., 480° C., 550° C., 580° C. and 650° C., with a predetermined actuating voltage applied thereto, as shown in Table to be described hereinafter.

Figure 6A:
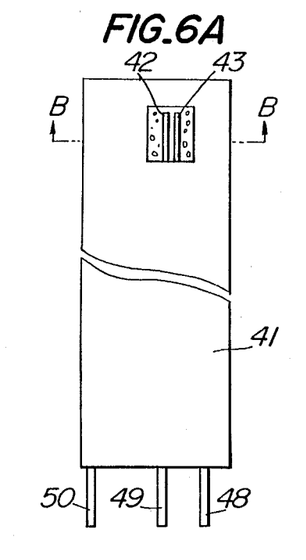

As shown in FIG. 6A, an opening 51 was bored, for instance by punching, through the green sheet for the cover ceramic layer 41 at such a position that, when the thus bored green sheet was overlaid on the green sheet for the ceramic substrate 40 so as to cover the entire pattern-printed surface of the latter sheet, the tip portions of the electrodes 42 and 43 were exposed to the outside through the opening 51. After being overlaid in the above manner, the green sheet for the cover ceramic layer 41 was joined to the green sheet for the ceramic substrate 40 by heating and pressing.

Thus, the printed patterns for the electrodes 42, 43 and the heater layer 44 were sandwiched between the green sheets for the ceramic substrate 40 and the cover ceramic layer 41, with the platinum lead wires 48 through 50 partially projecting to the outside of the thus joined green sheets and the tip portions of the electrodes 42 and 43 being exposed to the outside through the opening 51.

Granulated spherical ceramic particles (secondary particles) 52 with a grain size of 80–150 mesh, made of the same material as that of the above green sheets, were scattered through the opening 51 onto the exposed portion of the green sheet for the ceramic substrate 40 so as to be dispersed thereon in a single-particle layer. The green sheets with the ceramic particles 52 thus scattered thereon were heated in air at 1,500° C. for 2 hours. Whereby, the ceramic particles 52 were bonded to that surface portion of the ceramic substrate 40 which faced the opening 51 of the cover ceramic layer 41, as shown in FIG. 6C, so that such surface portion was roughened.

The thus bonded ceramic particles 52 formed projections 52a on the ceramic substrate 40 while defining recesses 52b therebetween. The cross-sectional area of the recess 52b in parallel to the plane of the ceramic substrate 40 increased with the depth thereof. Accordingly, when a thick film of gas-sensitive metal oxide paste was applied thereon as described hereinafter, bottom portion of such thick film intruded into such recesses 52b and the thick film is firmly bonded to the ceramic substrate 40, especially after being fired.

Figures 5B, 6B, 6C, 7B:
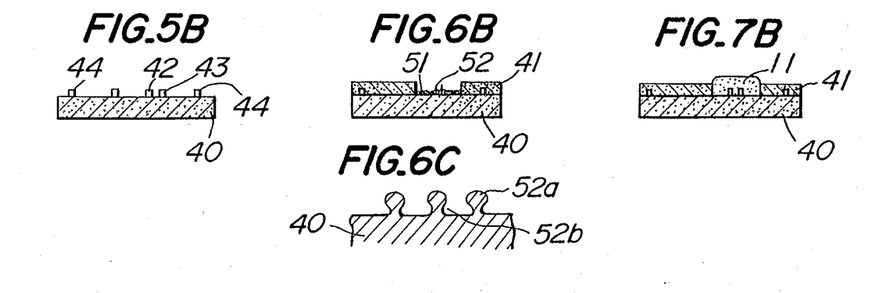
FIG. 6C is a fractional sectional view, showing granulated ceramic particles integrally bonded to a ceramic substrate so as to provide a roughened surface thereon.
Figure 7A:
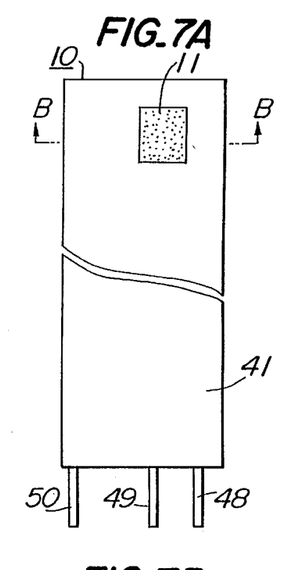

As shown in FIG. 7A and FIG. 7B, a gas-sensitive layer 11 was overlaid on the fired ceramic substrate 40 of each sample of the gas detector through the opening 51 of its cover ceramic layer 41. To this end, six kinds of titania paste were prepared in the following manner; namely, titania ($TiO_2$) powder having a mean diameter of 1.2 $\mu$m was mixed with platinum black at six different ratios, namely, 4, 6, 10, 20, 28 and 31 mole % based on the amount of titania; 3 wt% of ethyl cellulose based on the total of the powder mixture was added therein; and the mixture thus prepared was further mixed in BUTYL CARBITOL (a merchandise mark of 2-(2-butoxy ethoxy)ethanol) while controlling its viscosity so as to produce the titania paste having a viscosity of 300 poise.

The titania paste was applied to the opening 51 by the thick film techniques so as to fill up the opening 51 while ensuring tight contact of the tip portions of the electrodes 42 and 43 with the titania paste. The thickness of the titania paste layer thus applied was different for different groups of the samples as shown in Table to be described hereinafter. The samples with the titania paste applied thereon was fired at 1,200° C. in air for one hour, so that the gas-sensitive layer 11 with a porosity of 35%, falling in a preferable range of 20–45%, was formed as overlaid on the ceramic substrate 40. Whereby, samples of the gas sensor 10 according to the invention were completed.

Figure 8A:
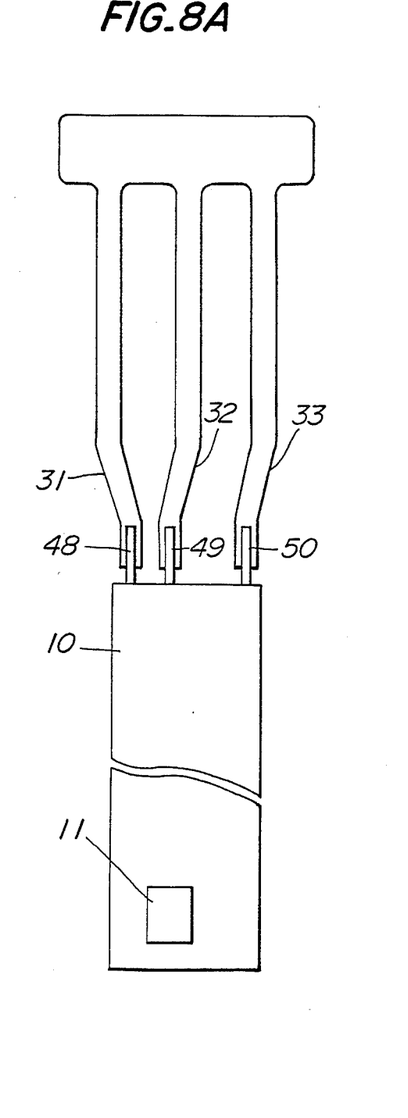
FIG. 8A is an explanatory diagram of the connections between lead wires and terminals.
Figure 8B:
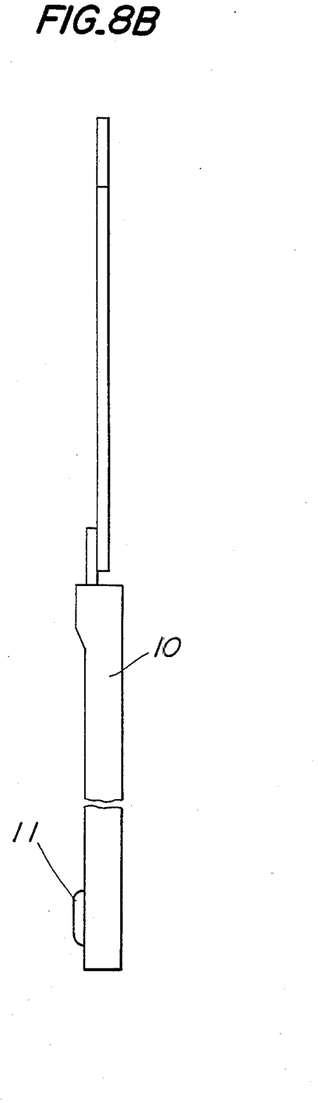
FIG. 8B is a side view of FIG. 8A.

The platinum lead wires 48 through 50 extending outwardly from the gas sensor 10 were connected to the terminals 31 through 33 respectively in a manner as shown in FIG. 8A. FIG. 8B shows a side view of the illustration of FIG. 8A.

Separately, the terminal 31 through 33 were made by etching a 0.5 mm thick nickel plate without severing them from each other as shown in FIG. 8A. The terminals 31 through 33 were brought in contact with the platinum lead wires 48 through 50 respectively, and the portions in contact with each other were bonded by spot welding. After the gas sensor 10 thus provided with the terminals was placed in the inner cylinder 14 carried by the body hardware 12 as shown in FIG. 2, the three terminal 31 through 33 were severed from each other at suitable portion so as to provide the terminals of certain lengths.

Twelve oxygen detectors, seven of them falling in the scope of the invention, were prepared in the manner explained above. All the oxygen sensors thus prepared had heater layers whose thickness and platinum black concentration were suitable for heating their gas-sensitive layers at specific temperature when placed in exhaust gas of 200° C. Experiments were made on the oxygen fuel ratio control of an actual internal combustion engine having an exhaust gas pipe on which the above oxygen detectors were mounted.

EXPERIMENTS

Experiments were carried out by using the above-referred twelve oxygen detectors and a conventional oxygen detector of zirconia type. The oxygen detectors were at first subjected to an endurance test by mounting them on the exhaust manifold of an internal combustion engine with a displacement of 2 l and running the engine for 30 hours at 5,600 r.p.m. ×4/4 (full open) with gasoline containing lead at a rate of 1.5 gram/gallon. Such condition for the endurance test represents a rather heavy duty involving consumption of that amount of gasoline which enables a regular car to run 10,000 km with leaded gasoline.

Figure 9:
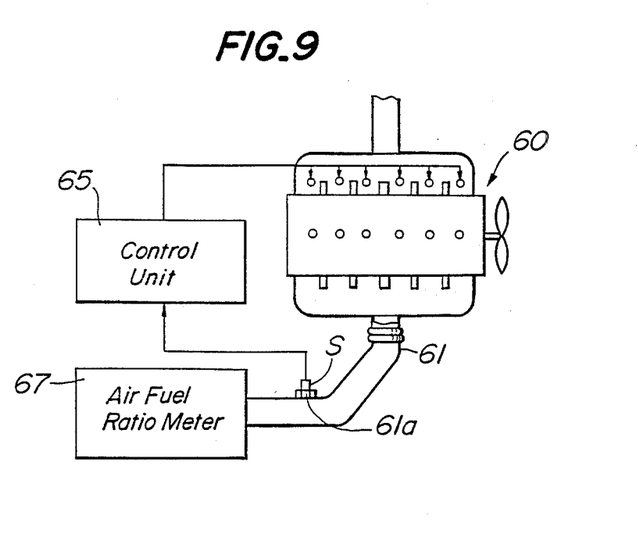
FIG. 9 is a diagrammatic illustration of the arrangement for an experiment of oxygen detectors mounted on the exhaust gas passage of an internal combustion engine.

Referring to FIG. 9, after the endurance test, each oxygen detector S was mounted on an engine exhaust pipe at a position 61a located 35 cm downstream of the exhaust manifold 61 of an internal combustion engine 60 which was similar to that of the endurance test. The output from the oxygen detector S was applied to a control unit 65 of an electronically controlled fuel injection system on the market. For each oxygen detector S, the engine 60 was run by using leadless gasoline while controlling the air fuel ratio under feedback control and while keeping the temperature of the engine exhaust gas at 200° C.

Figure 10:
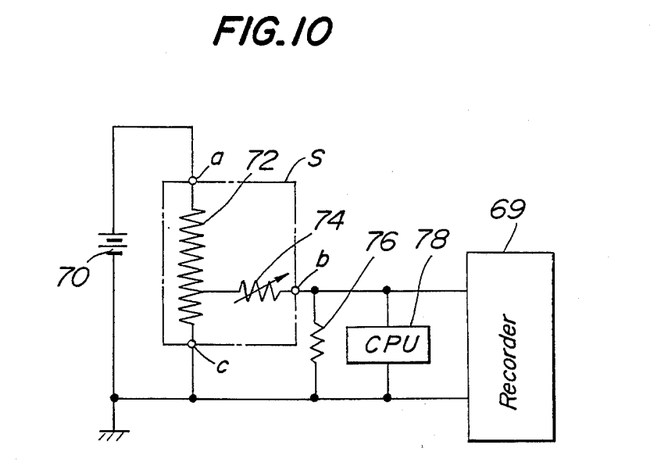
FIG. 10 is an electric circuit diagram of the experiment of FIG. 9.

The controlled air fuel ratio was measured by an air fuel ratio meter 67 of FIG. 9, and a control frequency F was measured by a recorder 69 of FIG. 10. The result is shown in Table.

TABLE

| Sample No. | Amount of Pt black (mole %) | Gas-sensor layer thickness ($\mu$m) | Gas-sensor layer temperature+ (°C.) | Control frequency F (Hz) | Air** fuel ratio A/F | Remark |
|---|---|---|---|---|---|---|
| S1 | 4.0 | 210 | 550 | 0.4 | 13.2 | — |
| S2 | 6.0 | 225 | 550 | 0.8 | 14.5 | * |
| S3 | 6.0 | 205 | 480 | 0.3 | 13.8 | — |
| S4 | 10.0 | 85 | 580 | *** | 12.0 | — |
| S5 | 10.0 | 120 | 580 | 1.1 | 14.7 | * |
| S6 | 10.0 | 250 | 580 | 1.2 | 14.6 | * |
| S7 | 10.0 | 320 | 580 | 1.2 | 14.6 | * |
| S8 | 10.0 | 410 | 580 | 0.6 | 14.6 | — |
| S9 | 10.0 | 250 | 650 | 1.1 | 14.6 | * |
| S10 | 20.0 | 250 | 580 | 0.8 | 14.6 | * |
| S11 | 28.0 | 250 | 580 | 0.7 | 14.6 | * |
| S12 | 31.0 | 250 | 580 | 0.5 | 14.8 | — |

TABLE-continued

| Sample No. | Amount of Pt black (mole %) | Gas-sensor layer thickness (μm) | Gas-sensor layer temperature+ (°C.) | Control frequency F (Hz) | Air** fuel ratio A/F | Remark |
|---|---|---|---|---|---|---|
| S13 | ZrO$_2$ type O$_2$ detector**** | | | *** | 12.0 | — |

Notes:
*falling in the scope of the invention
**controlled air fuel ratio
***uncontrollable
****zirconia type oxygen detector on the market
+within engine exhaust gas of 200° C.

The air fuel ratio meter 67 used was a LAMBDA SCAN made by RICARDO COMPANY. FIG. 10 schematically shows the electric circuit which was used in the experiments. A battery 70 rated at DC 14 volt was connected across the resistance 72 of the heater layer 44 of the oxygen detector S, and the resistance 74 of the gas-sensitive layer 11 was connected between an intermediate point of the resistance 72 and a terminal b of the oxygen detector S. The terminals a, b and c of FIG. 10 correspond to the terminals 31, 32 and 33 of FIG. 2 respectively. The current through the resistance 74 of the gas-sensitive layer 11 was introduced to a current-detecting resistance 76, and the voltage across the current-detecting resistance 76 was applied to a CPU 78 and the above-mentioned recorder 69. The CPU 78 was in the control unit 65 of FIG. 9.

The control frequency F was determined from the data of the recorder 69. The higher the control frequency F was, the quality of the control was better. In fact, the control frequency F is generally required to be larger than 0.7 Hz for practical purposes. In the internal combustion engine 60 used in the experiments, the optimal value of the controlled air fuel ratio A/F was 14.6±0.1 from the standpoint of the purifying efficiency of catalyst.

The result of the experiments will be reviewed now while considering the conditions that the control frequency be higher than 0.7 Hz and that the controlled air fuel ratio A/F be 14.6±0.1. The single-asterisked oxygen detector samples of Table, namely, the samples numbered S2, S5, S6, S7, S9, S10 and S11, met the above-mentioned two conditions. The concentration of platinum black the thickness of the gas-sensitive layer, and the temperature of the gas-sensitive layer will be reviewed in detail.

As to the concentration of platinum black, the sample S1 with the concentration of 4 mole % and the sample S12 with the concentration of 31 mole % did not meet the above two conditions. Accordingly, the range of the platinum black concentration for meeting the above conditions must be 5-30 mole %. If the concentration of platinum black is less than 4 mole %, it is likely that the gas-sensitive layer is poisoned by lead and its gas-sensitivity is deteriorated. On the other hand, if the concentration of platinum black is more than 31 mole %, the poisoning by lead is avoided but the response of the gas-sensitive layer becomes too slow.

As to the thickness of the gas-sensitive layer, the sample S4 with the thickness of 85 μm and the sample S8 with the thickness of 410 μm did not meet the above two conditions. Accordingly, the thickness of the gas-sensitive layer in a range of 100-400 μm meets the two conditions. If the gas-sensitive layer is thinner than 100 μm, it is likely deteriorated by lead, while if the gas-sensitive layer is thicker than 400 μm the diffusion distance for the gas therethrough becomes too long and its response becomes too slow.

As to the temperature of the gas-sensitive layer, the sample S3 with the temperature of 480° C. did not meet the above two conditions. Accordingly, it is necessary either to use the gas-sensitive layer at a temperature higher than 500° C. or to provide a heater capable of keeping the gas-sensitive layer a temperature higher than 500° C. If the temperature of the gas-sensitive layer is below 500° C., the platinum black contained therein is deteriorated by lead, and the catalytic activity of the gas-sensitive layer is reduced and its sensitivity is deteriorated.

In the embodiment described above, platinum is added in the gas-sensitive layer 11 in the form of platinum black. It is, however, possible to add platinum therein by a different method. For instance, the gas-sensitive layer 11 may be made porous, and a certain amount of platinum can be dispersed and deposited therein by dropping a solution of platinum, such as a solution of chloroplatinic acid, thereto, and drying and heating the layer 11.

As can be seen from the above embodiment and experiments, an excellent gas-sensor free from deterioration by lead can be provided by adding 5-30 mole % of platinum in the gas-sensitive layer thereof and making the thickness of the gas-sensitive layer 100-400 μm. If the gas-sensitive layer cannot be heated to a temperature above 500° C., a heater layer for heating the gas-sensitive layer must be provided.

For reference, a conventional zirconia type oxygen detector on the market was also tested as the sample S13 of Table. It was proved that such conventional oxygen detector was deteriorated by lead and could not provide satisfactory control of the air fuel ratio.

As described in the foregoing, a gas sensor according to the invention, which comprises a 100-400 μm thick gas-sensitive layer formed on a ceramic substrate and containing 5-30 mole % of a platinum group element or an alloy thereof, can maintain excellent gas-sensing ability without being deteriorated by lead even when used with an internal combustion engine run by leaded gasoline.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A gas sensor comprising a ceramic substrate, electrodes formed on said ceramic substrate, lead wires extending from said electrodes to outside of the gas sensor, and a 100-400 μm thick gas-sensitive layer formed on said ceramic substrate so as to sandwich said electrodes between said gas-sensitive layer and said substrate, which gas-sensitive layer contains 5-30 mole % of an ingredient selected from the group consisting of platinum group elements and alloys thereof and has an electric resistance depending on kind and concentration of a specific gas in atmosphere that is in contact with the gas-sensitive layer.

2. A gas sensor as set forth in claim 1, wherein said ceramic substrate has a roughened surface facing said gas-sensitive layer, said roughened surface having 80-150 mesh granulated ceramic particles integrally sintered thereto so as to form recesses between adjacent particles, said particles being made of the same ceramics as that of the substrate, said gas-sensitive layer having projections meshing with said recesses.

3. A gas sensor as set forth in claim 1, wherein said ingredient of the gas-sensitive layer is platinum.

4. A gas sensor as set forth in claim 1, wherein said gas-sensitive layer contains an oxide semiconductor as a major ingredient thereof.

5. A gas sensor as set forth in claim 3, wherein said oxide semiconductor is titania ($TiO_2$).

6. A gas sensor as set forth in claim 1, wherein said gas sensor further comprises a heater layer secured to the ceramic substrate so as to heat the gas-sensitive layer.

7. A gas sensor as set forth in claim 6, wherein said heater layer is adapted to heat said gas-sensitive layer to a temperature higher than 500° C.

* * * * *